(12) United States Patent
Haab

(10) Patent No.: US 7,077,653 B2
(45) Date of Patent: Jul. 18, 2006

(54) DENTAL SCALER FOR USE IN CLEANING TEETH OF ORTHODONTIC PATIENTS

(76) Inventor: Debra M Haab, 2701 E. Bucher Dr., Syracuse, IN (US) 46567

( * ) Notice: Subject to any disclaimer, the term of this patent is extended or adjusted under 35 U.S.C. 154(b) by 4 days.

(21) Appl. No.: 10/924,663

(22) Filed: Aug. 24, 2004

(65) Prior Publication Data

US 2006/0046228 A1    Mar. 2, 2006

(51) Int. Cl.
*A61C 17/00*    (2006.01)
(52) U.S. Cl. ..................................... 433/143
(58) Field of Classification Search ............ 433/3, 433/141, 143; 132/328, 329; 606/84; D24/146, D24/149, 152
See application file for complete search history.

(56) References Cited

U.S. PATENT DOCUMENTS

| | | | | |
|---|---|---|---|---|
| 1,402,525 A | * | 1/1922 | Moseler | 433/143 |
| 1,503,610 A | * | 8/1924 | Smith | 433/143 |
| 3,309,773 A | | 3/1967 | Weller | |
| 4,167,063 A | | 9/1979 | Sosnay | |
| D259,660 S | | 6/1981 | Sosnay | |
| 4,597,398 A | | 7/1986 | Chu | |
| D301,962 S | | 7/1989 | Huang | |
| 5,004,419 A | * | 4/1991 | Kline | 433/143 |
| 5,388,989 A | | 2/1995 | Kountis | |
| D359,122 S | | 6/1995 | Kountis | |
| 6,322,362 B1 | * | 11/2001 | Holms | 433/143 |

FOREIGN PATENT DOCUMENTS

EP    366624 A2  *  5/1990

OTHER PUBLICATIONS

Dental Supply Catalogues, 15 pages, undated.
"Design Features of the Shank", Instrument Design and Classification, pp. 183-194. undated.

* cited by examiner

*Primary Examiner*—Ralph A. Lewis
*Assistant Examiner*—Casey Donahoe
(74) *Attorney, Agent, or Firm*—Baker & Daniels LLP

(57) ABSTRACT

A dental scaler for cleaning teeth having an orthodontic appliance. The scaler includes a handle with at least one scaling portion having a scaling element. The scaling portion of the device consists of a plurality of sections connected by a plurality of angles and is designed to permit the scaling element to fit between a brace wire and a tooth.

27 Claims, 5 Drawing Sheets

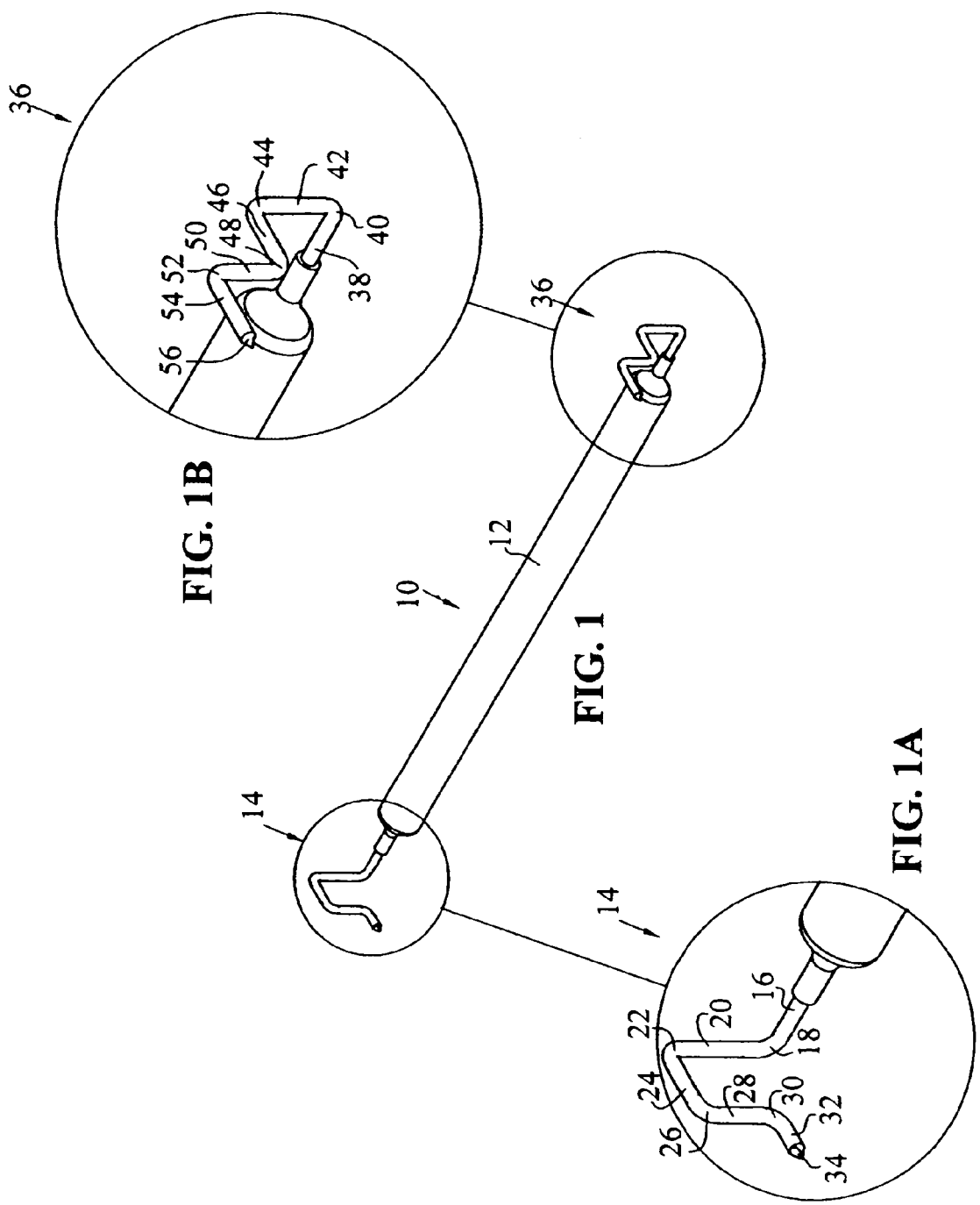

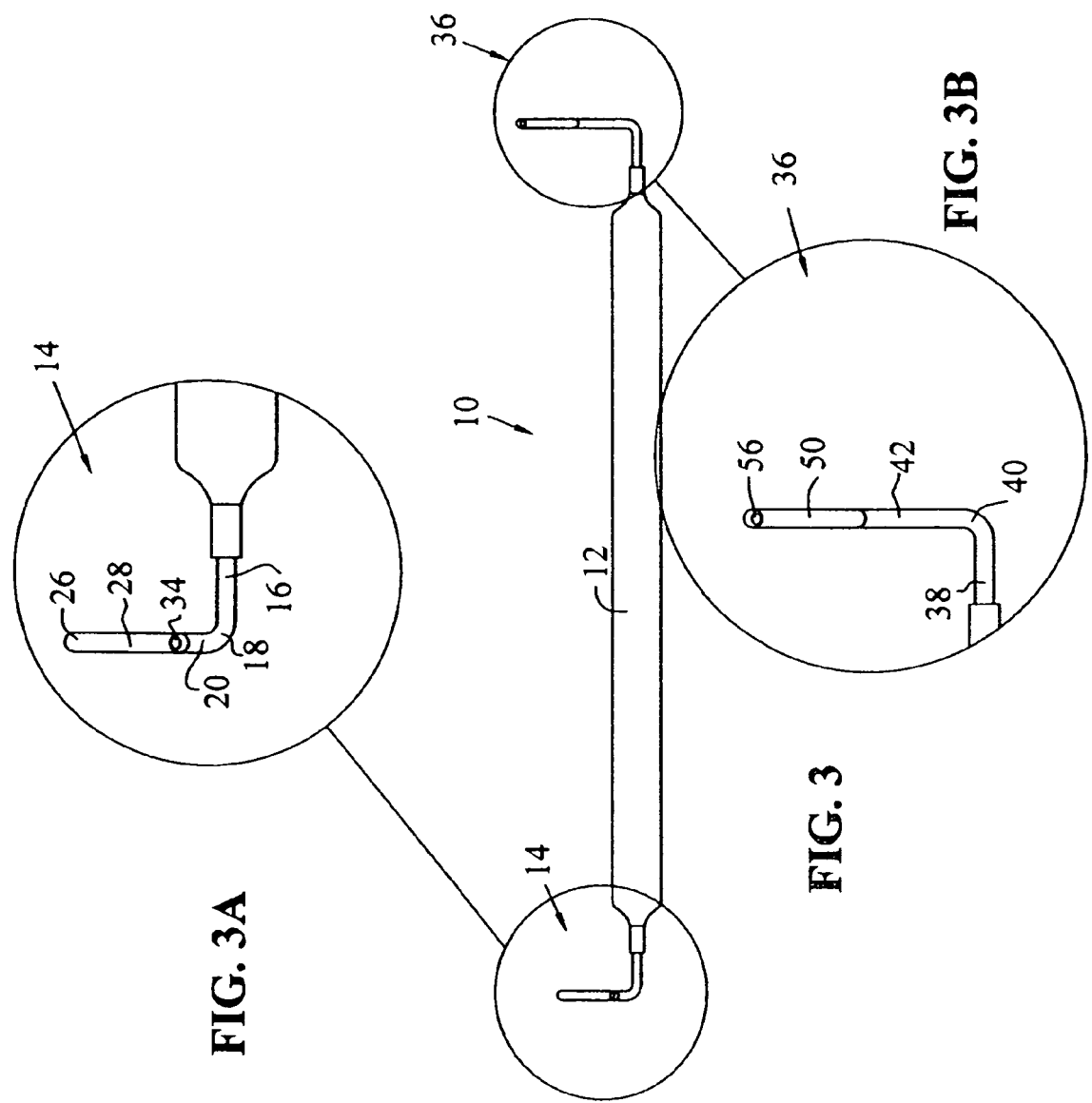

DENTAL SCALER FOR USE IN CLEANING TEETH OF ORTHODONTIC PATIENTS

FIELD OF THE INVENTION

The invention generally relates to a dental scaler, and in particular, to a dental scaler having a configuration designed to navigate around an orthodontic appliance.

BACKGROUND OF THE INVENTION

There are various instruments in the dental art for cleaning teeth. One such device that is well known to remove plaque and tartar from teeth is a dental scaler. Typical scalers consist of a handle having an attached scaling portion with a scaling element. In use, a dentist or hygienist, positions the scaling element against a tooth and scrapes away tartar and plaque. Due to variations in the contour of the dental table, several scalers with different scaling portions are required to fully and effectively clean all of a patient's teeth.

When a patient has an orthodontic appliance, the task of effectively positioning the scaling element to clean a tooth is even more difficult. In addition to the variations in the contour of the dental table, the dentist must navigate around a brace wire and exercise care so as to not scrape off a brace bracket. While numerous different scaling portions exist, none are generally designed for cleaning around orthodontic appliances.

One prior art device is shown in U.S. Pat. Nos. 5,388,989 and Des. 359,122 to Kountis, which are incorporated in their entirety herein by reference. This device is designed to clean every part of the occlusal table. The device disclosed by Kountis includes a handle with a scaling portion having a scaling element. Due to the positioning of the scaling element on the scaling portion, it is apparent that the scaling device disclosed by Kountis is not generally designed for use with patients having an orthodontic appliance, and the specification does not contemplate such a use.

Another prior art device is disclosed in U.S. Pat. No. Des. 301,962 to Huang, which is incorporated in its entirety herein by reference. This device consists of a hook with a rotatable handle and is presumably used for cleaning teeth although no disclosure or teaching is provided thereof. As with Kountis, it is evident that the location of the tip of the scaling portion is not generally designed to effectively clean a patient's teeth while navigating around an orthodontic appliance, and there is no teaching or disclosure for such.

SUMMARY OF THE INVENTION

The present invention relates to a dental scaler having a handle, a scaling portion, and a scaling element. The scaling portion connects the scaling element to the handle in a manner that allows the scaling element to efficiently and effectively clean teeth having an orthodontic appliance attached.

In an embodiment of the present invention, the handle has a scaling portion affixed to each end. In addition, either of the scaling portions may be detachable from the handle. Further, in an embodiment of the present invention, the handle may be rotatable about its central axis.

In an embodiment of the present invention, the scaling portion includes at least five sections connected by a plurality of angles. The first section protrudes from the handle and runs along the central axis of the handle. The second section extends from the first and is perpendicular to the central axis of the handle. The third section extends from the second section at a right angle away from the handle. The fourth section extends from the third section and is parallel to the second section. The fifth section extends from the fourth section and is parallel to the third section. In this embodiment, the fifth section connects the fourth section and the scaling element.

Also, in an embodiment of the present invention, a second scaling portion includes at least five sections connected by a plurality of angles. The first section protrudes from the handle and runs along the handle's central axis. The second section extends from the first and is perpendicular to the central axis of the handle. The third section extends from the second section at a right angle toward the handle. The fourth section extends from the third section and is parallel to the third section. The fifth section extends from the fourth section and is parallel to the second section. In this embodiment, the fifth section connects the fourth section and the scaling element.

In another embodiment of the present invention, a dental scaler is provided for use in cleaning teeth of patients having an orthodontic appliance and includes a handle portion having a generally central axis extending along the length thereof; and a scaling portion affixed to either end of the handle portion and which has at least five sections and at least four angles. The scaling portion may include a first section protruding from the handle portion along the axis thereof, a second section extending at a first angle from the first section, a third section extending from the second section at a second angle such that the first section is at an angle to a plane defined by the second and third sections, a fourth section extending from the third section at a third angle, and a fifth section extending from the fourth section at an angle with the fifth section having a scaling element at the end thereof.

The dental scaler may include a scaling portion affixed to each end of the handle portion. The scaling portion may be detachable from the handle portion, and the handle portion may be rotatable.

The second, third, fourth, and fifth sections of the scaling portion define a plane in one embodiment, and the second section may be perpendicular to the central axis of the handle portion. The third and fifth sections of the scaling portion may be generally parallel to one another, and the fourth section may extend from the third section away from the handle portion. The fourth section may extend from the third section so that it is generally anti-parallel to the second section.

In an additional embodiment of the invention, a dental scaler is provided for use in cleaning the teeth of patients having an orthodontic appliance and includes a handle portion having a generally central axis extending along the length thereof; and a scaling portion having at least five sections and being affixed to either end of the handle portion. The scaling portion may include a first section protruding from the handle portion along the axis thereof, a second section extending at an angle from the first section and being generally perpendicular to the central axis of the handle portion, a third section extending from the second section at an angle away from the handle portion, a fourth section extending from the third section at an angle, and a fifth section extending from the fourth section at an angle, and being generally parallel to the third section. The fifth section has a scaling element at an end thereof.

The dental scaler may be provided wherein the scaling portion is detachable from the handle portion, and the handle portion may be rotatable.

In another embodiment of the invention, a dental scaler is provided that may be used in cleaning teeth of patients with an orthodontic appliance and that includes a handle portion having a generally central axis extending along the length thereof; and a scaling portion having five sections that is affixed to either end of the handle portion with the scaling portion including a first section protruding from the handle along the axis thereof, a second section extending from the first section at an angle, a third section extending from the second section at an angle, a fourth section extending from the third section at an angle and being generally anti-parallel to the second section, and a fifth section extending from the fourth section at an angle and being generally parallel to the third section, and the fifth section has a scaling element at the end thereof.

The dental scaler may be detachable from the handle portion, and the handle portion may be rotatable.

In one embodiment of the invention, a dental scaler is provided for use in cleaning teeth of patients having an orthodontic appliance, wherein the dental sclaer includes a handle portion having a generally central axis extending along the length thereof; and a scaling portion comprised of five sections that is affixed to either end of the handle portion, and the scaling portion includes a first section protruding from the handle portion along the axis thereof, a second section extending at an angle from the first section and being generally perpendicular to the central axis of the handle portion, a third section extending from the second section at an angle, a fourth section extending from the third section at an angle and being generally parallel to the second section, and a fifth section extending from the fourth section at an angle, the fifth section having a scaling element at an end thereof.

The scaling portion may be detachable from the handle portion, and the handle portion may be rotatable.

The dental scaler may also include a second scaling portion affixed to the end of the handle portion opposite the first scaling portion that includes a first section protruding from the handle portion, a second section extending from the first section at an angle, a third section extending from the second section at an angle, a fourth section extending from the third section at an angle such that it is generally anti-parallel to the second section, and a scaling element at an end thereof. The scaling portions may be detachable from the handle portion, and the handle portion may be rotatable.

In a further embodiment of the invention, a dental scaler is provided for use in cleaning teeth of patients having an orthodontic appliance that includes a handle portion having a generally central axis extending along the length thereof; and a scaling portion affixed to either end of the handle portion and having at least four sections including a first section connected to the handle portion, a second section connected to and extending from the first section at a first angle thereto, a third section connected to and extending from the second section at an angle thereto, the third section being parallel to the first section, and a fourth section connected to said third section at an angle thereto, the fourth section being parallel to the second section and having a scaling element at the end thereof.

The four sections of the dental scaler may lie in a common plane, and the plane may be perpendicular to the central axis of the handle portion. The third section may be anti-parallel to the first section. The dental scaler may further include a fifth section interconnecting the first section and the handle portion.

In yet another embodiment of the invention, a dental scaler is provided for use in cleaning teeth of patients having an orthodontic appliance, wherein the dental scaler includes a handle portion having a generally central axis extending along the length thereof; and a scaling portion affixed to either end of the handle portion that includes a plurality of sections connected by angles, and at least two or more of the sections are perpendicular to the axis of the handle portion. The dental scaler may include at least three sections with at least two of the sections interconnected by a third section so that the two sections are parallel to one another.

Further features of the present invention will become apparent from the detailed description contained herein. However, it should be understood that the detailed description, and specific examples, while indicating embodiments of the invention, are given by way of illustration only, since various changes and modifications within the spirit and scope of the invention will become apparent to those skilled in the art.

BRIEF DESCRIPTION OF THE DRAWINGS

The above-mentioned and other features of this invention will become more apparent and the invention itself will be better understood by reference to the following description of embodiments of the present invention taken in conjunction with the accompanying drawings, wherein:

FIG. 1 is a perspective view of a dental scaler designed to clean teeth having an orthodontic appliance;

FIG. 1A is a close up perspective view of one end of the dental scaler of FIG. 1 from the area indicated;

FIG. 1B is a close up perspective view of the other end of the dental scaler of FIG. 1 from the area indicated;

FIG. 3A is a side view of the scaler of FIG. 1A;

FIG. 3B is a side view of the scaler of FIG. 1B;

Figure 4:
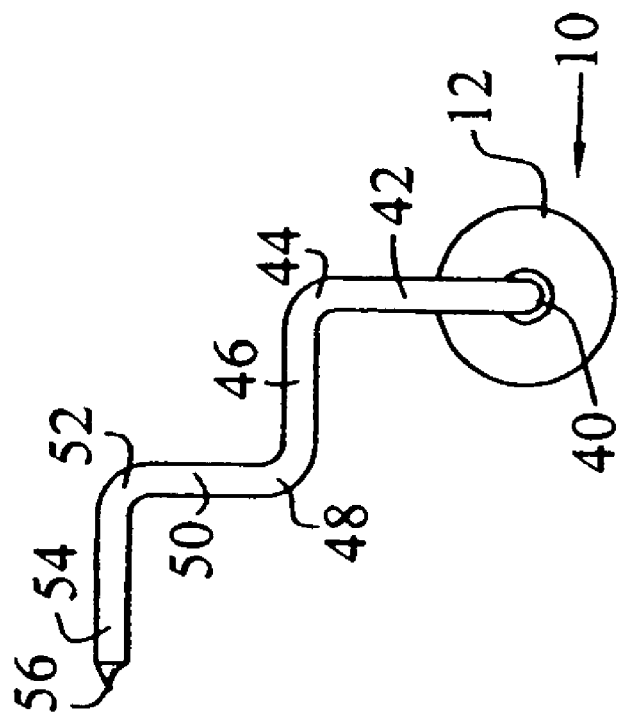
FIG. 4 is an end view of the scaler of FIG. 1B.

Corresponding reference characters indicate corresponding parts throughout the several views. Although the drawings represent embodiments of the present invention, the drawings are not necessarily to scale and certainly features may be exaggerated in order to better illustrate and explain the present invention. The exemplification set out herein illustrates embodiments of the invention and such exemplifications are not to be construed as limiting the scope of the invention in any manner.

DETAILED DESCRIPTION OF EMBODIMENTS OF THE INVENTION

For the purposes of promoting an understanding of the principles of the invention, reference will now be made to the embodiments illustrated in the drawings, which are described below. It will nevertheless be understood that no limitation of the scope of the invention is thereby intended. The invention includes any alterations and further modifications in the illustrated devices and described methods and further applications of the principles of the invention which would normally occur to one skilled in the art to which the invention relates.

Now referring to FIG. 1, a dental scaler for cleaning the teeth of a patient having an orthodontic appliance is shown generally indicated as 10. The dental scaler 10 includes a handle 12 with scaling portions generally indicated as 14 and 36 affixed to opposite ends of the handle 12. In the embodiment shown, dental scaler 10 is assembled as a unitary structure, however, it is possible to manufacture dental scaler 10 such that scaling portions 14 and 36 are detachable from the handle 12.

In this embodiment, handle portion 12 is cylindrical with a generally central axis. In a preferred embodiment, handle portion 12 is comprised of a non-corrosive metal and has a surface conducive for gripping. Handle 12 may be made using a forging, molding, or other known process. Also, it is foreseeable to make handle 12 rotatable.

Figure 2:
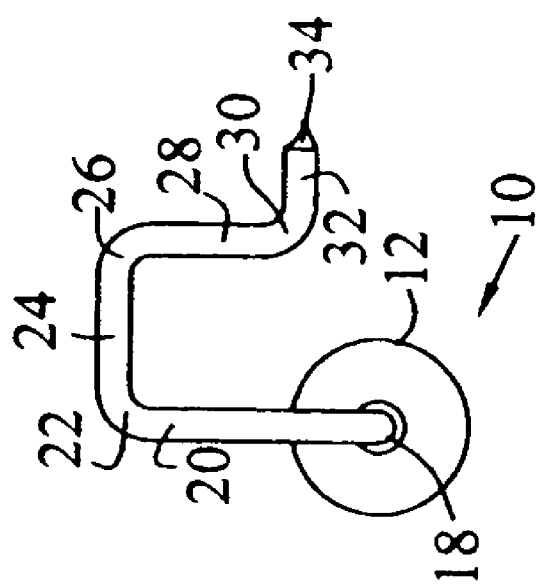
FIG. 2 is an end view of the scaler of FIG. 1A.

Now referring to FIGS. 1A, 2 and 3A, scaling portion 14 is shown. Scaling portion 14 is comprised of five sections 16, 20, 24, 28, 32, four angles 18, 22, 26, 30, and a scaling element 34. The first section 16 protrudes from the handle 12 along the axis thereof. The second section 20 extends from the first section 16 at an angle 18 and is connected to the third section 24 via angle 22. The fourth section 28 extends from the third section 24 at an angle 26 and is connected to the fifth section 32 via angle 30. Fourth section 28 also extends antiparallel to section 20. Scaling element 34 is formed at the free end of fifth section 32. Section 32 extends parallel to section 24. In the embodiment shown, angles 18, 22, 26 and 30 are right angles. Further, it is preferable for sections 20, 24, 28, and 32 to define a plane that is generally perpendicular to a plane defined by sections 20 and 16. Scaling portion 14 is preferably formed from a rigid non-corrosive metal wire that is hard enough to function as a scaler and can be sterilized.

Now referring to FIGS. 1B, 3B, and 4, the second scaling portion 36, is shown. Scaling portion 36 consists of five sections 38, 42, 46, 50, 54, four angles 40, 44, 48, 52, and a scaling element 56. First section 38 protrudes from the handle 12 along the axis thereof. Second section 42 extends from the first section 38 at an angle 40 and is connected to the third section 46 via angle 44. The fourth section 50 extends from the third section 46 via angle 48 and is connected to the fifth section 54 via angle 52. Formed at the end of the fifth section 54 is scaling element 56. In the embodiment of the dental scaler shown, angles 40, 44, 48 and 52 are all right angles. Also, section 50 is parallel to section 42, and section 54 is parallel to section 46. Further, it is desirable for sections 42, 46, 50 and 54 to define a plane that is perpendicular to a plane defined by sections 38 and 42. Scaling portion 36 is also preferably formed from a rigid non-corrosive metal wire that is hard enough to function as a scaler and can be sterilized.

Figure 5:
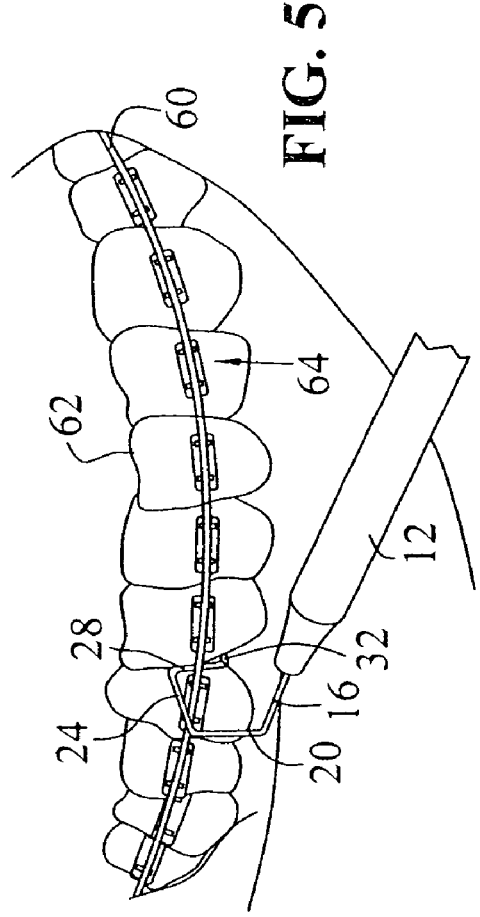
FIG. 5 depicts the scaler end of FIG. 1A in use.

Now referring to FIG. 5, scaling portion 14 of dental scaler 10 is shown in use for cleaning teeth 62 having an orthodontic appliance generally indicated as 64 with a brace wire 60 extending between the teeth. To use dental scaler 10, the handle portion 12 is grasped and scaling portion 14 is positioned over the brace wire 60 such that section 24 runs over brace wire 60 and is generally perpendicular to the tooth being cleaned. When properly positioned, scaling element 34 is against a tooth or between two teeth 62 and handle portion 12 is in a position to be grasped and manipulated by an operator for cleaning the teeth. Since handle 12 is perpendicular to section 32 having scaling element 34, the scaling portion can be maneuvered to reach every tooth. Accordingly, as clearly demonstrated in FIG. 5, scaling portion 14 provides a novel and effective means for cleaning around an orthodontic appliance.

Figure 6:
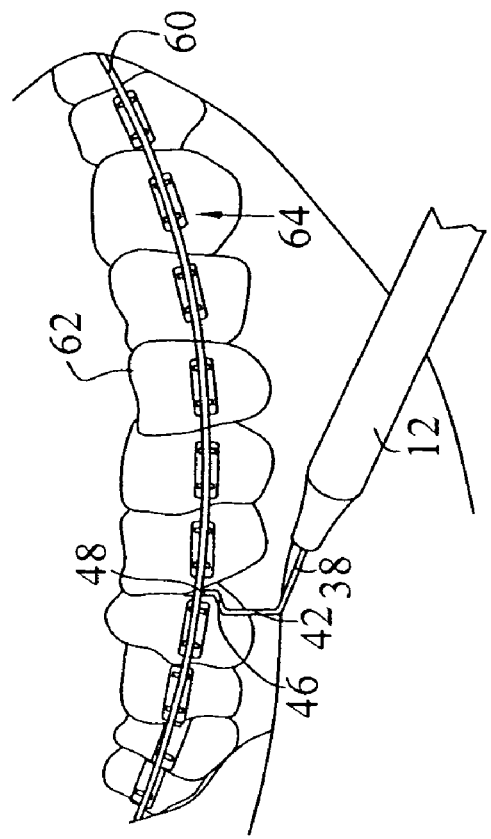
FIG. 6 depicts the scaler end of FIG. 1B in use.
Figure 7:
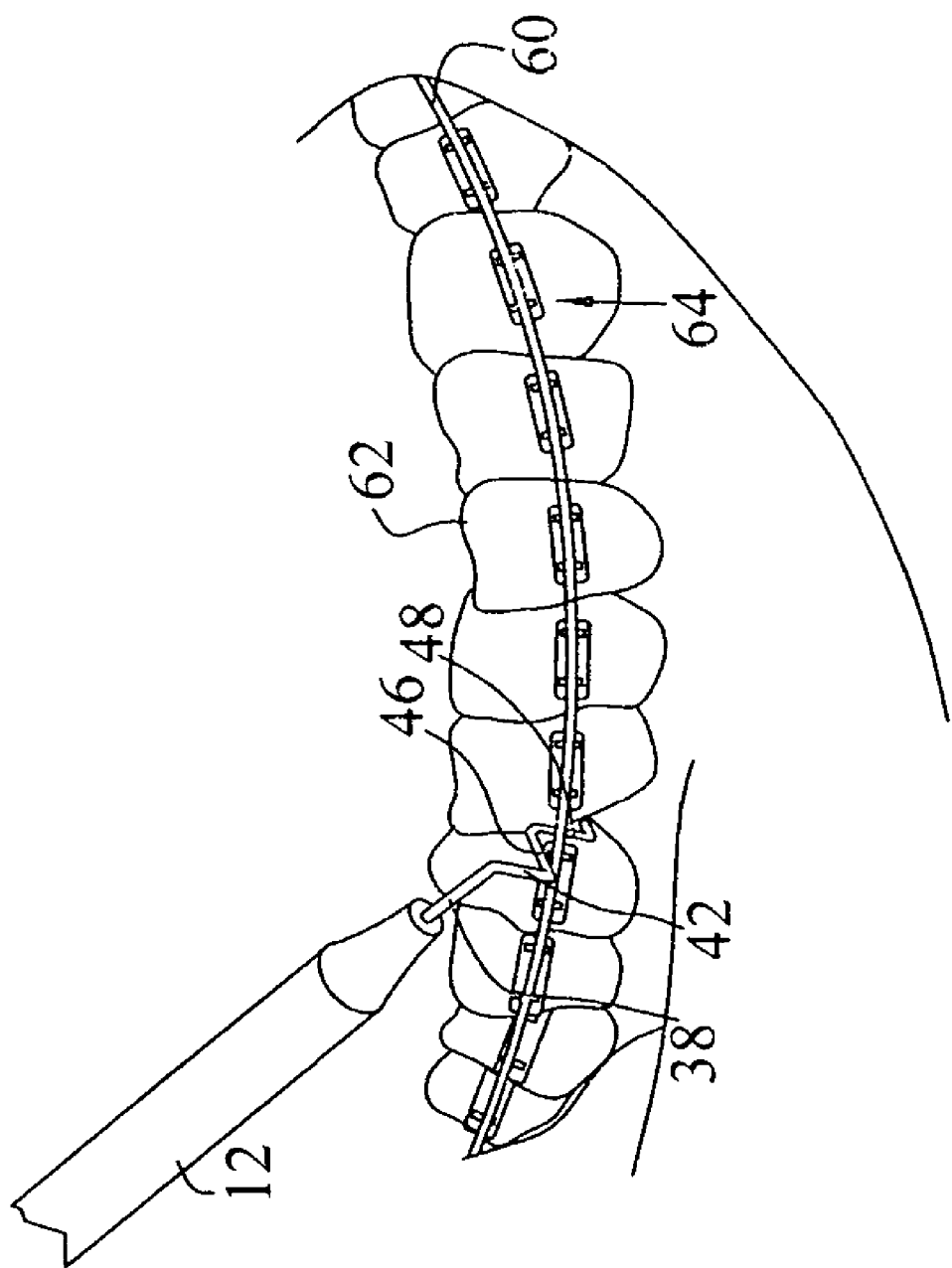
FIG. 7 depicts the scaler end of FIG. 1B in use in another manner.

With reference now to FIGS. 6 and 7, scaling portion 36 of dental scaler 10 is shown in use for cleaning teeth 62 having orthodontic appliance 64. To use scaling portion 36, the handle 12 is grasped and section 50 of scaling portion 36 is positioned between the brace wire 60 and teeth 62. When properly positioned, scaling element 56 is against a tooth or between teeth 62, and handle 12 is in a position to be grasped for cleaning teeth 62. Since handle 12 is perpendicular to section 54 having scaling element 56, scaling portion 36 can be maneuvered to reach every tooth.

While the invention has been taught with specific reference to the above embodiments, one skilled in the art will recognize that changes can be made in form and detail without departing from the spirit and scope of the invention. For example, the dental scaler may be made of materials other than metal. Additionally, although a unitary design offers certain manufacturing efficiencies, it is also possible to make the device out of multiple parts that may be adhered or otherwise joined together. Furthermore, the general shape of the handle 12 and scaling portions can be varied into any configuration suitable to performing the above described procedure. It should also be understood that the term "angles" as used herein to describe the transition between different sections of the scaling portions includes bends and radiuses or any other type of transition so that adjoining sections are not aligned with one another. As such, the described embodiments are to be considered in all respects as illustrative only and not restricted. The scope of invention is, therefore, indicated by the following claims rather than by the description or drawings.

What is claimed is:

1. A dental scaler for use in cleaning teeth of patients having an orthodontic appliance, comprising:
   a handle portion having a generally central axis extending along the length thereof; and
   a scaling portion affixed to either end of said handle portion having at least five sections and at least four angles, including a first section protruding from said handle portion along the axis thereof,
   a second section extending at a first angle from said first section,
   a third section extending from said second section at a second angle such that said first section is at an angle to a plane defined by said second and third sections,
   a fourth section extending from said third section at a third angle, and
   a fifth section extending from said fourth section at an angle with said fifth section having a scaling element at the end thereof, and said fifth section is generally parallel to said third section.

2. The dental scaler of claim 1, wherein said handle has a scaling portion affixed to each end.

3. The dental scaler of claim 1, wherein said scaling portion is detachable from said handle portion.

4. The dental scaler of claim 1, wherein said handle portion is rotatable.

5. The dental scaler of claim 1, wherein said second, third, fourth, and fifth sections of said scaling portion define a plane.

6. The dental scaler of claim 5, wherein said second section is perpendicular to the central axis of the handle portion.

7. The dental scaler of claim 1, wherein said fourth section extends from said third section away from said handle portion.

8. The dental scaler of claim 1, wherein said fourth section extends from said third section generally anti-parallel to said second section.

9. A dental scaler for use in cleaning teeth of patients having an orthodontic appliance, comprising:
   a handle portion having a generally central axis extending along the length thereof; and a scaling portion having at least five sections and being affixed to either end of said handle portion, including
  a first section protruding from said handle portion along the axis thereof,
  a second section extending at an angle from said first section and being generally perpendicular to the central axis of said handle portion,
  a third section extending from said second section at an angle away from said handle portion, said second and third sections lying in a plane that is at an angle to said central axis,
  a fourth section extending from said third section at an angle, and
  a fifth section extending from said fourth section at an angle and being generally parallel to said third section, said fifth section having a scaling element at an end thereof.

10. The dental scaler of claim 9, wherein said scaling portion is detachable from said handle portion.

11. The dental scaler of claim 9, wherein said handle portion is rotatable.

12. A dental scaler for use in cleaning teeth of patients with an orthodontic appliance, comprising:
  a handle portion having a generally central axis extending along the length thereof; and
  a scaling portion including five sections that is affixed to either end of said handle portion, including
    a first section protruding from said handle portion along the axis thereof,
    a second generally straight linear section extending from said first section at an angle,
    a third generally straight linear section extending from said second section at an angle,
    a fourth generally straight linear section extending from said third section at an angle and being generally anti-parallel to said second section, and
    a fifth section extending from said fourth section at an angle and being generally parallel to said third section, said fifth section having a scaling element at the end thereof.

13. The dental scaler of claim 12, wherein said scaling portion is detachable from said handle portion.

14. The dental scaler of claim 12, wherein said handle portion is rotatable.

15. A dental scaler for use in cleaning teeth of patients having an orthodontic appliance, comprising:
  a handle portion having a generally central axis extending along the length thereof; and
  a scaling portion including five sections that is affixed to either end of said handle portion, including
    a first section protruding from said handle portion along the axis thereof,
    a second section extending at an angle from said first section and being generally perpendicular to the central axis of said handle portion,
    a third section extending from said second section at an angle,
    a fourth section extending from said third section at an angle and being generally parallel to said second section, and
    a fifth section extending from said fourth section at an angle, said fifth section having a scaling element at an end thereof.

16. The dental scaler of claim 15, wherein said scaling portion is detachable from said handle portion.

17. The dental scaler of claim 15, wherein said handle portion is rotatable.

18. The dental scaler of claim 15, further including a second scaling portion affixed to the end of said handle portion opposite said first scaling portion, including
  a first section protruding from said handle portion,
  a second section extending from said first section at an angle,
  a third section extending from said second section at an angle,
  a fourth section extending from said third section at an angle such that it is generally anti-parallel to said second section, and
  a scaling element at an end thereof.

19. The dental scaler of claim 18, wherein either of said scaling portions are detachable from said handle portion.

20. The dental scaler of claim 18, wherein said handle portion is rotatable.

21. A dental scaler for use in cleaning teeth of patients having an orthodontic appliance, said dental scaler comprising:
  a handle portion having a generally central axis extending along the length thereof; and
  a scaling portion affixed to either end of said handle portion and having at least four sections, including,
    a first section connected to said handle portion,
    a second section connected to and extending from said first section at a first angle thereto,
    a third section connected to and extending from said second section at a second angle thereto, said third section being parallel to said first section, and
    a fourth section connected to said third section at a third angle thereto, said fourth section being parallel to said second section and having a scaling element at the end thereof, said four sections of said dental scaler lying in a common plane that is perpendicular to the central axis of the handle portion.

22. The dental scaler of claim 21, wherein said third section is antiparallel to said first section.

23. The dental scaler of claim 21, further including a fifth section interconnecting said first section and said handle portion.

24. A dental scaler for use in cleaning teeth of patients having an orthodontic appliance, the dental scaler comprising:
  a handle portion having a generally central axis extending along the length thereof; and
  a scaling portion affixed to either end of said handle portion including a plurality of sections connected by angles, at least two of which are right angles and at least two or more of said sections being perpendicular to the axis of said handle portion.

25. A dental scaler for use in cleaning teeth of patients having an orthodontic appliance, the dental scaler comprising:
  a handle portion having a generally central axis extending along the length thereof; and
  a scaling portion affixed to either end of said handle portion including a plurality of sections connected by angles, including at least three sections and wherein at least two of said sections are interconnected by a third section so that said two sections are parallel to one another, at least two or more of said sections being perpendicular to the axis of said handle portion.

26. A dental scaler for use in cleaning teeth of patients having an orthodontic appliance, the dental scaler comprising:
  a handle portion having a generally central axis extending along the length thereof; and a scaling portion affixed to either end of said handle portion including a plurality of sections connected by angles, at least two or more sections including straight linear portions and at least two or more sections are perpendicular to the axis of said handle.

27. A dental scaler for use in cleaning teeth of patients having an orthodontic appliance, comprising:
 a handle portion having a generally central axis extending along the length thereof; and
 a scaling portion affixed to either end of said handle portion having at least five sections and at least four angles, including
  a first section protruding from said handle portion along the axis thereof,
  a second section extending at a first angle from said first section,
  a third section extending from said second section at a second angle such that said first section is at an angle to a plane defined by said second and third sections,
  a fourth section extending from said third section at a third angle, and
  a fifth section extending from said fourth section at an angle with said fifth section having a scaling element at the end thereof, and at least three of said sections having generally straight portions.

* * * * *